US010919857B2

(12) United States Patent
Sinha et al.

(10) Patent No.: US 10,919,857 B2
(45) Date of Patent: Feb. 16, 2021

(54) OLIGO-GUANIDINES BASED CELLULAR TRANSPORTER COMPRISING HETEROCYCLIC RINGS WITH HYDROPHOBIC AND/OR LIPOPHILIC GROUPS AT N-TERMINAL FOR EFFECTIVE DELIVERY OF NONPENETRABLE CARGOS IN-VITRO AND IN-VIVO

(71) Applicant: INDIAN ASSOCIATION FOR THE CULTIVATION OF SCIENCE, Kolkata (IN)

(72) Inventors: Surajit Sinha, Kolkata (IN); Jhuma Bhadra, Kolkata (IN); Sankha Pattanayak, Kolkata (IN); Jayanta Kundu, Kolkata (IN)

(73) Assignee: INDIAN ASSOCIATION FOR THE CULTIVATION OF SCIENCE, Kolkata (IN)

( * ) Notice: Subject to any disclaimer, the term of this patent is extended or adjusted under 35 U.S.C. 154(b) by 0 days.

(21) Appl. No.: 16/065,485

(22) PCT Filed: Jun. 10, 2016

(86) PCT No.: PCT/IN2016/000150
§ 371 (c)(1),
(2) Date: Jun. 22, 2018

(87) PCT Pub. No.: WO2017/109789
PCT Pub. Date: Jun. 29, 2017

(65) Prior Publication Data
US 2019/0002408 A1    Jan. 3, 2019

(30) Foreign Application Priority Data

Dec. 23, 2015 (IN) .......................... 1328/KOL/2015

(51) Int. Cl.
| | | |
|---|---|---|
| C07D 211/58 | (2006.01) | |
| A61K 47/18 | (2017.01) | |
| A61K 9/00 | (2006.01) | |
| A61K 47/54 | (2017.01) | |
| A61K 31/7088 | (2006.01) | |
| C12N 15/113 | (2010.01) | |

(52) U.S. Cl.
CPC .......... *C07D 211/58* (2013.01); *A61K 9/0019* (2013.01); *A61K 31/7088* (2013.01); *A61K 47/183* (2013.01); *A61K 47/545* (2017.08); *C12N 15/113* (2013.01); *C12N 2310/11* (2013.01); *C12N 2310/351* (2013.01); *C12N 2320/32* (2013.01)

(58) Field of Classification Search
CPC .............. C07D 211/58; A61K 2300/00; A61K 2300/90019; A61K 31/7088; A61K 47/545; C12N 15/113; C12N 2310/351; C12N 2310/3233; C12N 2310/323; C12N 15/111
See application file for complete search history.

(56) References Cited

U.S. PATENT DOCUMENTS

| | | |
|---|---|---|
| 2007/0078078 A1 | 4/2007 | Hou et al. |
| 2008/0221020 A1 | 9/2008 | Goodman et al. |
| 2012/0296087 A1 | 11/2012 | Sinha et al. |

OTHER PUBLICATIONS

Pattanayak et al., A cationic morpholino antisense oligomer conjugate: synthesis, cellular uptake and inhibition of Gli1 in the hedgehog signalling pathway, RSC Advances, vol. 4, pp. 1951-1954. (Year: 2014).*
International Search Report for PCT/IN2016/000150 dated Nov. 16, 2016.

* cited by examiner

*Primary Examiner* — Dana H Shin
(74) *Attorney, Agent, or Firm* — The PL Law Group, PLLC

(57) ABSTRACT

An oligo-guanidine as cell penetrating agents/carriers includes a heterocyclic ring including 4-aminopiperidine, piperazine, morpholine having at least one N-terminal based heterocyclic ring or at least one O-heteroatom based heterocyclic ring tailored with hydrophobic and/or lipophilic group. The oligo-guanidine is adapted as an effective molecular transporter to transport and/or delivery therapeutics, therapeutic candidates, probes, or other molecules of interest across biological barriers including oligonucleotides. Advantageously, the oligo-guanidine is capable of being internalized into cells (in-vitro and in-vivo) with enhanced cellular uptake in nanomolar concentration.

2 Claims, 7 Drawing Sheets

Specification includes a Sequence Listing.

FIG. 1

Indian patent application no. 71/KOL/2013 dated 21 January 2013

Yolk injected Zebrafish with 4c

Control zebrafish

Uniform distribution of 4c in zebrafish injected embryos

FIG.5

Control zebrafish a: No tail dependent phenotypes b: Gene Tools vivo morpholino injected phenotypes (a) 4a-conjugated morpholinos, (b) Commercially available vivo morpholinos Figure 6. Structures of Morpholinos, Vivo Morpholinos and 4a-morpholinos

$R_2$= Me, Et, n-Pr, i-Pr, t-Bu, hexafluoroisopropyl, octyl 2-hexyldecyl $R_3$=Bz, Fmoc, Alloc, CbZ
Base=Et$_3$N, DIPEA, DIPA, DBU, TMEDA

Scheme 1: Synthesis of transporters

FIG. 8

Scheme 2: Type 2 transporter

SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: MORPHOLINOS SEQUENCE 25 mer

<400> SEQUENCE: 1
gacttgaggc agacatattt ccgat                                    25

OLIGO-GUANIDINES BASED CELLULAR TRANSPORTER COMPRISING HETEROCYCLIC RINGS WITH HYDROPHOBIC AND/OR LIPOPHILIC GROUPS AT N-TERMINAL FOR EFFECTIVE DELIVERY OF NONPENETRABLE CARGOS IN-VITRO AND IN-VIVO

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/IN2016/000150, filed Jun. 10, 2016, which claims priority to the benefit of India Patent Application No. 1328/KOL/2015 filed in the India Intellectual Property Office on Dec. 23, 2015, the entire contents of which are incorporated herein by reference.

FIELD OF INVENTION

The present invention relates to oligo-guanidines based cellular transporter comprising heterocyclic rings including 4-aminopiperidine, piperazine, morpholine having at least one N-terminal based heterocyclic ring or at least one O-heteroatom based heterocyclic ring tailored with hydrophobic and/or lipophilic group and related compounds adapted as cell penetrating agents/carriers, and also relates to its method of preparation. Advantageously, said oligo-guanidines are adapted as effective molecular transporters for transport and/or delivery of therapeutics, therapeutic candidates, probes, or other molecules of interest across biological barriers including oligonucleotides. Advantageously, said oligo-guanidines comprising at least one modified N-terminal with hydrophobic or lipophilic chain are capable of being internalized into cells (in-vitro and in-vivo) with enhanced cellular uptake in nanomolar concentration in the presence of 10% serum-containing media with ideally no toxicity upto 100 µM concentration favouring end use and application for intercellular delivery of a cargos, including but not limited to a drug, drug candidate, probe or other molecules of interest. It effectively internalizes in vivo into zebrafish model.

BACKGROUND ART

The cellular delivery of a molecule of interest such as a drug, a diagnostic agent, a probe can be achieved or enhanced by electrostatically or covalently attaching the molecule of interest to a molecular transporter compound having guanidinium functional groups. The cellular uptake property can be a function of the number and/or orientation of guanidinium groups on the molecular transporter compound. Many guanidinium-rich compounds including peptides and dendrimers show cell penetrating properties and used to deliver cargos inside cells, The landmark work of Frankel et al. (Frankel, A. D.; Pabo, C. O. Cell 1988, 55, 1189) taught that HIV-1 transactivator of transcription (Tat) protein is able to penetrate cellular membranes. Further studies identified the presence of guanidinium-containing arginine amino acid in Tat as responsible for penetration property. Since then, a variety of cell penetrating peptides (CPPs) or protein transduction domains have been described to deliver cargo inside cells. Many authors have reviewed the use and mechanism of CPPs in detail (Lindgren, M et al. Trends Pharmacol. Sci. 2000, 21, 99 and Richard, 3. P. et al. 3. Biol. Chem. 2003, 278, 585 and Heitz, F. Br J Pharmacol. 2009, 157, 195).

Reference is drawn to P. A. Wender et al. in Proc. Natl. Acad. Sci. U.S.A. 2000, 97, 13003 and Org. Lett. 2001, 3, 3229 which discloses octaarginine as an octa-peptide of arginine that is being extensively used to deliver cargos, including drugs and antisense oligonucleotides inside cell.

However, synthesis of guanidinium-rich peptides and dendrimers are difficult and expensive. The bioavailability of the said peptides is usually limited, attributed to in vivo proteolysis by various endogenous peptidases. Other problems are uncertain in vivo delivery efficiency, potential neurotoxicity and immunogenicity. Presence of too many flexibly attached guanidinium groups in such carriers develops toxicities, nonspecific interactions or hydrolyzed by peptidases in the case of CPPs. Several other alternatives have thus been described which contain non-peptide backbones (Chung, S.-K. et al. Int. J. Pharm. 2008, 354, 16). Wender et al. taught oligocarbonate molecular transporters (Cooley et al. in 3. Am. Chem. Soc. 2009, 131, 16401) whereas J. Valero et al. in Org. Biomol. Chem., 2012, 10, 5417 illustrates the use of chiral bicyclic guanidinium oligomers as cell penetrating motifs.

G. Lättig-Tünnemann et al. in Nat. Commun. 2011, 2:453 has taught the role of backbone rigidity and static orientation of guanidinium groups for enhanced cellular uptake of the molecular transporters involving guanidine, however, the exact internalization mechanism and minimum necessary features required to impart cellular penetration properties by different vectors are still in debate. The molecular transporters known till date contain little structural resemblances; however, net positive charge is found to be essentially required in almost all cases.

Reference is drawn to co-pending Indian patent application no. 71/KOL/2013 dt. 21 January 2013 that discloses internally substituted oligoguanidiniums (FIG. 1) for cellular transfection at 2.5 µM concentration and also discloses its facile synthetic procedure.

Hence based on the necessary requirement of a net positive charge of the (cell penetrating peptides) CPP's for cellular penetration properties, backbone rigidity and static orientation, it is also imperative to have simple molecular transporter to be synthesized with ease and with minimum functional groups to handle suitable for diverse range of applications of the molecular transporter to deliver therapeutic agents and probes inside cell that would also have a balance of hydrophilicity and hydrophobicity or would essentially have amphipathic character for effective cellular transport and would also be less toxic for useful application.

As apparent from the aforesaid it is thus the need of the day to explore new and useful molecular transporters with a net positive charge which while on one hand would have a facile process of synthesis and on the other hand would also provide for backbone rigidity, static orientation and amphipathic character with a balance between hydrophilic and hydrophobic character for enhanced cellular uptake together with reduced toxicity.

SUMMARY

It is thus a primary object of the present invention to provide for guanidine based oligomers and related compounds that are hydrophobically and/or lipophilically tailored as cell penetrating agents/carriers and its method of preparation thereof that would be adapted as efficient molecular transporters for transport and/or delivery of therapeutics, therapeutic candidates, probes, or other molecules of interest across biological barriers including oligonucleotides but not limited to them.

It is another object of the present invention to provide for said guanidine based oligomers with net positive charge with a minimum numbers of guanidinium groups, that would be linked into conformationally rigid backbone and static orientation for increased cellular penetration properties and enhanced cellular uptake with a modification by hydrophobic group to have an amphipathic character and would also be capable of pre-organizing itself during penetration through cell membrane in solution phase.

It is yet another object of the present invention to provide for a process of preparation of said guanidine based oligomers in solution that would involve concise process steps with high yields that would also involve minimum number of functional groups to handle to thereby be a facile process that would be industrially favourable to find diverse range of applications to deliver therapeutic agents and probes inside cell.

It is still another object of the present invention to provide for conjugates of said oligo-guanidines involving conjugates with morpholino-based antisense, peptides, therapeutic agents such as cancer drugs including paclitaxel and doxorubicin also including conjugates with oligonucleotides and its method of preparation thereof.

It is another object of the present invention to provide for said oligo-guanidines and its conjugates that would also be adapted for encapsulation for effective delivery inside the cells.

The present invention is described hereunder in reference to the following non-limiting examples and accompanying figures which are merely illustrative and are not to be construed as a limitation of scope of the present invention.

BRIEF DESCRIPTION OF THE DRAWINGS

(a) and (b) of FIG. 5: illustrates zebrafish image of compound 4a conjugated morpholinos and commercially available Gene Tool vivo morpholino injected respectively.

DETAILED DESCRIPTION

Thus according to the basic aspect of the present invention there is provided oligo-guanidines as cell penetrating agents and carriers comprising heterocyclic ring conjugated internally substituted oligomeric guanidines including selectively hydrophobic and/or lipophilic group with said hydrophobic and/or lipophilic group disposed in a well defined 3D structure in solution phase as a 6 member ring with selective positioning of the guanidinium into energetically favourable equatorial orientations enabling cellular permealization.

Preferably said oligo-guanidines are provided wherein said hydrophobic and/or lipophilic group is in N-terminal of a heterocyclic ring or is adjacent to O-heteroatom of the terminal heterocyclic ring.

More preferably said oligo-guanidines is provided with adaptibility for linkage to molecules including biomolecules to favour transport and delivery of said molecules inside a cell.

According to another preferred aspect of the present invention there is provided said oligo-guanidines wherein said heterocyclic ring having hydrophobic and/or lipophilic group in its N-terminal is linked to another heterocyclic ring having covalently conjugated said molecules in its N-terminal, through repetitive guanidinium moiety.

According to yet another preferred aspect of the present invention there is provided said oligo-guanidines wherein said internally substituted oligomeric guanidines involve guanidinium moieties conjugated to anyone or more heterocyclic rings including 4-aminopiperidine, piperazine, morpholine.

Preferably, in said oligo-guanidines said guanidinium moieties are derived of 4-aminopiperidine and piperazine heterocyclic rings.

Preferably in said oligo-guanidines said guanidinium moieties are derived of morpholine based heterocyclic rings.

According to another preferred aspect of the present invention there is provided said oligo-guanidines wherein said oligomeric guanidines comprise Type 1 oligos comprising six membered 4-amino piperidines interconnected through guanidinium linkages having the following representative structure as hereunder:

Type 1 oligoguanidine transporters wherein $R_1$=hydrophobic and/or lipophilic group, R=non-penetrable cargos for delivery.

According to yet another preferred aspect of the present invention there is provided said oligo-guanidines wherein said oligomeric guanidines comprise Type 2 oligos comprising six membered morpholine interconnected through guanidinium linkages having the following representative structure as hereunder:

Type 2 oligoguanidine transporters wherein $R_1$=azide or hydrophobic and/or lipophilic group, R=non-penetrable cargos for delivery.

Preferably in said oligo-guanidines said $R_1$ being hydrophobic and/or lipophilic group is amphipathic in character including tert-butyloxycarbonyl (t-BOC), hexafluoro-isopropyloxycarbonyl [i-Pr(F)], n-octyloxycarbonyl (n-OOC), 2-hexyl-1-decyloxycarbonyl (HDOC), methoxycarbonyl (MeOC), ethoxycarbonyl (EtOC), propoxycarbonyl (POC), iso-propoxycarbonyl (IPOC); and wherein R is a molecule for delivery inside the cells that include biomolecules fluorophores, oligonucleotides, peptides, diagnostic agent, probes, antisense agents, drugs including cancer drugs.

More preferably in said oligo-guanidines the value of "n" varies from at least 2 or more depending upon transfection efficiency of said oligomer with molecules for delivery inside cells.

According to another preferred aspect of the present invention there is provided said oligo-guanidines as efficient cell penetrating agents and carriers that efficiently internalizes in the cell in the levels of at least 95-100% at very low concentrations of at least about 50 nM and is free of toxicity upto the levels of 100 μM.

According to another aspect of the present invention there is provided a process for the synthesis of oligo-guanidines comprising providing selectively hydrophobic and/or lipophilic group for covalent linkage in N-terminal of heterocyclic ring conjugated internally substituted oligomeric guanidines or providing hydrophobic and/or lipophilic group for covalent linkage adjacent to O-heteroatom of the terminal heterocyclic ring conjugated internally substituted oligomeric guanidines;

such that said hydrophobic and/or lipophilic groups are disposed in a well defined 3D structure in solution phase as a 6 member ring with selective positioning of the guanidinium into energetically favourable equatorial orientations and obtaining therefrom said oligo-guanidines.

Preferably said process for the synthesis of oligo-guanidines is provided comprising providing internally substituted oligomeric guanidines having one heterocyclic ring based N-terminal or internally substituted oligomeric guanidines having O-heteroatom based terminal heterocyclic ring for tailoring with hydrophobic and/or lipophilic group either at said N-terminal or adjacent to said O-heteroatom of the terminal heterocyclic ring; and covalently linking the same through repetitive guanidinium moieties to another heterocyclic ring based N-terminal for covalent linkage to molecules to obtain therefrom said oligo-guanidines adapted as cell penetrating agents and carriers for transporting and delivering said molecules inside a cell.

More preferably said process for the synthesis of oligo-guanidines as Type 1 transporters comprises (a) providing heterocyclic ring based secondary amine preferably piperzine that is protected carbamate including hydrophobic and/or lipophilic group and is also trityl protected for reaction/coupling with another heterocyclic ring preferably 4-amino piperidine that is thiourea and trityl protected primary amine monomer and obtaining a trityl protected dimer;

(b) trityl deprotection of the dimer for further reaction with said monomer to finally obtain an oligomer with trityl protection on last added monomer and with protected guanidinium moieties as internally substituted oligomeric guanidine Type 1 transporter therefrom.

More preferably said process for the synthesis of oligo-guanidines as Type 2 transporters comprises (a) providing heterocyclic ring based secondary amine preferably morpholine that is protected with carbamate including hydrophobic and/or lipophilic group and is also trityl protected for reaction/coupling with another heterocyclic ring preferably morpholine that is thiourea and trityl protected primary amine monomer and obtaining a trityl protected dimer;

(b) trityl deprotection of the dimer for further reaction with said monomer to finally obtain an oligomer with trityl protection on last added monomer and with protected guanidinium moieties as internally substituted oligomeric guanidine as Type 2 transporter therefrom.

According to yet another preferred aspect of the present invention a process for the synthesis of oligo-guanidines is provided including (c) deprotection step for deprotecting the trityl group on the last added monomer in said oligomer and conjugating the same with a molecule including biomolecule and finally deprotecting the guanidinium moiety post conjugation to obtain therefrom said oligo-guanidines as cell penetrating agents and carriers.

Preferably in said process for the synthesis of oligo-guanidines said step (a) comprises providing said carbamate in trifluoroethanol that was reacted with acetic acid at 0° C. and stirred for about half an hour to result in an amine that is reacted with protected thiourea monomer to get the dimer;

said step (c) comprises conjugating trityl deprotected free amine with a molecule preferably BODIPY dye (4,4-Difluoro-5,7-dimethyl-4-bora-3a,4a-diaza-s-indacene) through the reaction with BODIPY-NHS (N-hydroxysuccinimide ester of BODIPY) ester in presence of base in a solvent mixture preferably dichloromethane-acetonitrile.

According to yet another preferred aspect of the present invention in said process for the synthesis of oligo-guanidines as claimed said thiourea protected primary amine monomer includes protection by Bz (benzoyl), Fmoc (Fluorenylmethyloxycarbonyl), Alloc (allyloxycarbonyl), CbZ (benzyloxycarbonyl) and wherein the base employed is $Et_3N$ (triethylamine), DIPEA (diisopropylethylamine), DIPA (diisopropylamine), DBU (diazabicycloundecene), TMEDA (tetramethylethylenediamine).

According to another aspect of the present invention a method of transporting molecules including biomolecules in a cell is provided comprising the steps of (a) providing oligo-guanidines comprising heterocyclic ring conjugated internally substituted oligomeric guanidines including selectively hydrophobic and/or lipophilic group disposed in a well defined 3D structure in solution phase as a 6 member heterocyclic ring with selective positioning of the guanidinium into energetically favourable equatorial orientations enabling cellular permealization said hydrophobic and/or lipophilic group preferably disposed in N-terminal of a heterocyclic ring or adjacent to O-heteroatom of the terminal heterocyclic ring;

(b) linking to molecules including biomolecules for transporting and delivering said molecules inside a cell.

As discussed herein before the present invention provides oligo-guanidines as cell penetrating agents/carriers adapted as a cellular transporter for delivering drug and therapeutics including oligonucleotides inside cells and also provides a simple facile process for preparation of the same.

The oligo-guanidines of the present invention includes oligo-guanidine oligomers that are amphipathic in nature attributed to the combination of hydrophobic or lipophilic groups including tert-butyloxycarbonyl [t-BOC], hexafluoro-iso-propyloxycarbonyl [i-Pr(F)] and polar guanidinium groups which is surprisingly found to be very efficient in delivering cargos as per the in vivo illustration in zebrafish model.

In one embodiment of the present invention there is provided rigid backbone based internally substituted cationic oligo-guanidine molecules (Type 1 and 2 in FIG. 2), comprising internally substituted guanidines and heterocyclic rings such as 4-aminopiperidine, piperazine, morpholine in which either one N-terminal is modified with hydrophobic or lipophilic group or an adjacent position of O-heteroatom based heterocyclic ring in the terminal is modified with hydrophobic or lipophilic group, and related compounds as cell penetrating agents/carriers that pre-organizes itself in a well defined 3D structure in solution phase; with the molecule having 6 member ring that can position the guanidinium into energetically favourable equatorial orientations.

Another embodiment of the present invention provides conjugates of said oligo-guanidines involving conjugates with peptides, therapeutic agents such as cancer drugs including paclitaxel and doxorubicin also including conjugates with oligonucleotides that is chemically conjugated to one amine-end of said oligomers of the present invention for effective and enhanced delivery inside cells.

The oligo-guanidine based carrier/penetrating agent of the present invention advantageously find its end use and application as cellular delivery agents (in vitro study) and employed in vivo zebrafish model.

Thus in one aspect of the present invention, there is provided Type 1 (3, 4 of FIG. 2) oligomers where the guanidinium moieties are constituted by 4-aminopiperidine and piperazine rings.

In another aspect of the present invention, there is provided Type 2 (5 of FIG. 2) oligomers where the guanidinium moieties comprise morpholino rings.

Figure 2:
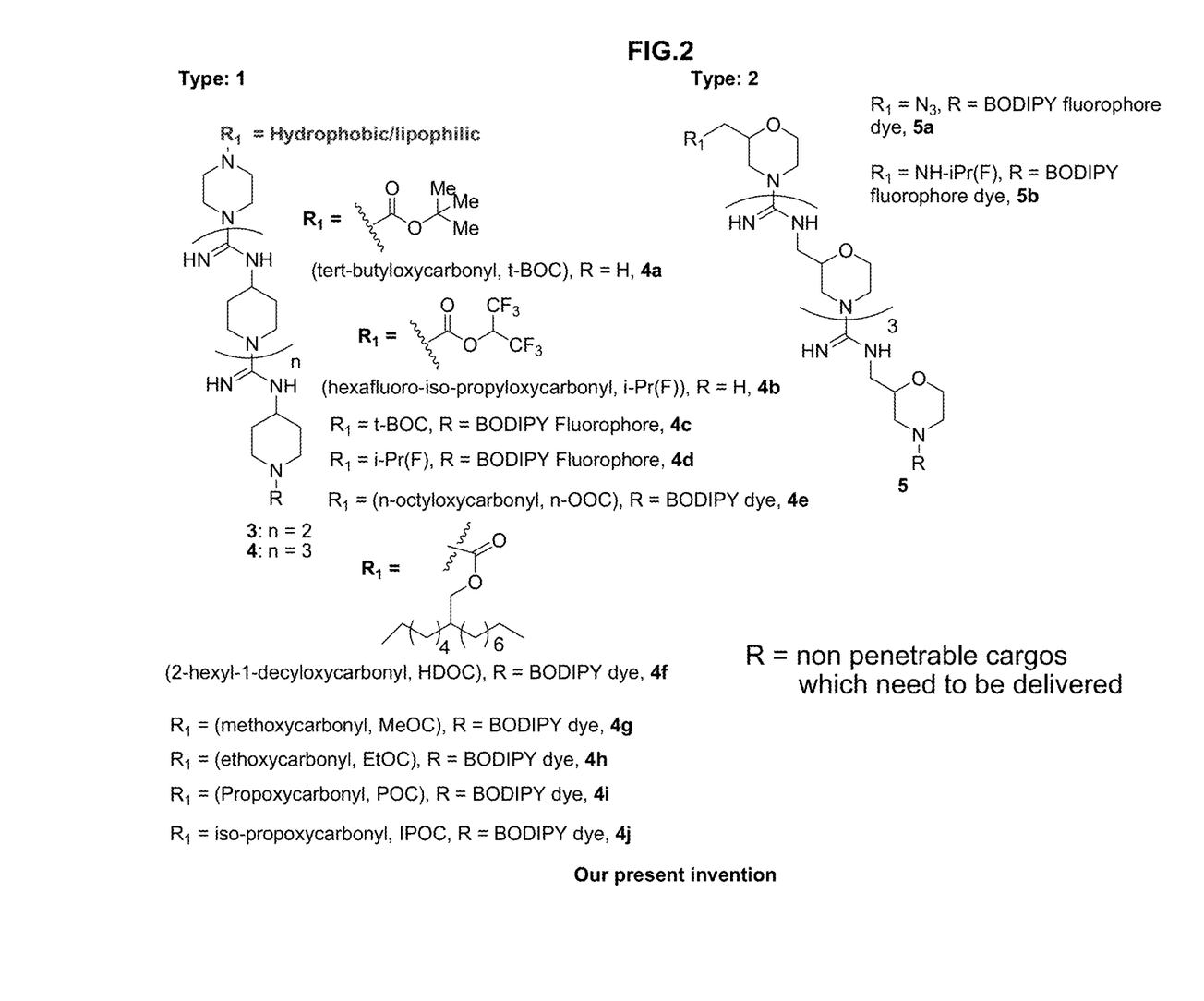
FIG. 2: illustrates oligo-guanidines based cellular transporter having at least one N-terminal modified with hydrophobic or lipophilic group or at least one O-heteroatom based heterocyclic ring at the terminal modified with hydrophobic or lipophilic group at the position adjacent to said O-heteroatom.

In a preferred embodiment shown in FIG. 2, the functional oligomeric guanidinium compound constitutes the Type 1 oligo which is constituted of six membered 4-amino piperidines interconnected through guanidinium linkages.

The length of the cationic oligomers may vary, wherein the value of "n" varies from at least 3 or more depending upon the ease of preparation and encapsulation efficiency of the said oligomer with oligonucleoties to deliver it inside cells.

Advantageously, the guanidinium oligomers comprise one amine terminus for covalent attachment with other biomolecules of interest. R in FIG. 2 represent fluorophores, oligonucleotides, peptides and drugs but are not limited to them.

According to another embodiment of the present invention there is provided internally substituted oligo-guanidines as cell penetrating agents/carriers that is encapsulated with a conjugate selected from peptides, therapeutic agents such as cancer drugs including paclitaxel and doxorubicin also including conjugates with oligonucleotides for delivery inside the cells.

CHO-K1, PC-3, A-549, MCF-7 Cells:

Chinese hamster ovary (CHO-K1) cells were obtained from cell repository NCCS, Pune. The cells were regularly maintained in DMEM medium (Gibco) supplemented with 10% FBS (Gibco), 100 µg/mL streptomycin and 100 units/mL penicillin and incubated at 37° C. in a humidified atmosphere of 5% $CO_2$.

MCF-7 cells: Human breast adenocarcinoma MCF-7 cells were obtained from ATCC. MCF-7 cells were regularly cultured in DMEM supplemented with 10% FBS, 100 µg/mL streptomycin and 100 units/mL penicillin in a similar way as mentioned in case of CHO-K1 cells.

PC-3 cells: Human prostate cancer cell line PC-3 was obtained from cell repository NCCS, Pune. PC-3 cells were cultured regularly in F12K nutrient mixture (Gibco) supplemented with 10% FBS and 100 µg/mL streptomycin and 100 units/mL penicillin. For subculture, they were trypsinized with 0.25% trypsin-EDTA.

A549 (human non small cell lung cancer) cell lines were obtained from cell repository NCCS, Pune. A549 cells were cultured in F12K nutrient mixture supplemented with 10% Fetal Bovine Serum (FBS), streptomycin and penicillin.

Example 1: Comparative Study of Efficacy and Toxicity

Figure 1:
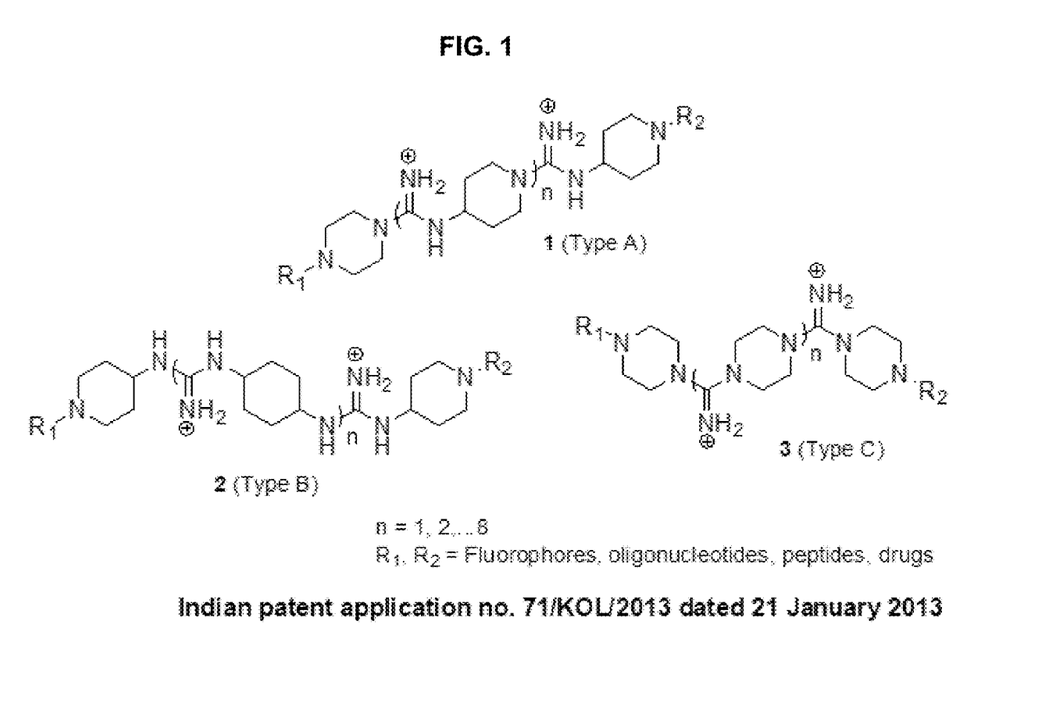
FIG. 1: illustrates oligo-guanidines as cell penetrating agents of Type A, Type B, type C as disclosed in the co-pending 71/KOL/2013.

It is a significant finding of the present invention that when at least one N-terminal of piperazine ring of the transporter of FIG. 1 is tailored to have a hydrophobic or lipophilic group, a new molecule exemplified as molecule 3 or 4 of FIG. 2 resulted with remarkably increase in efficacy of cellular transfection to upto 100% internalization at the concentration levels of only 150 nM under similar conditions.

Figure 3:
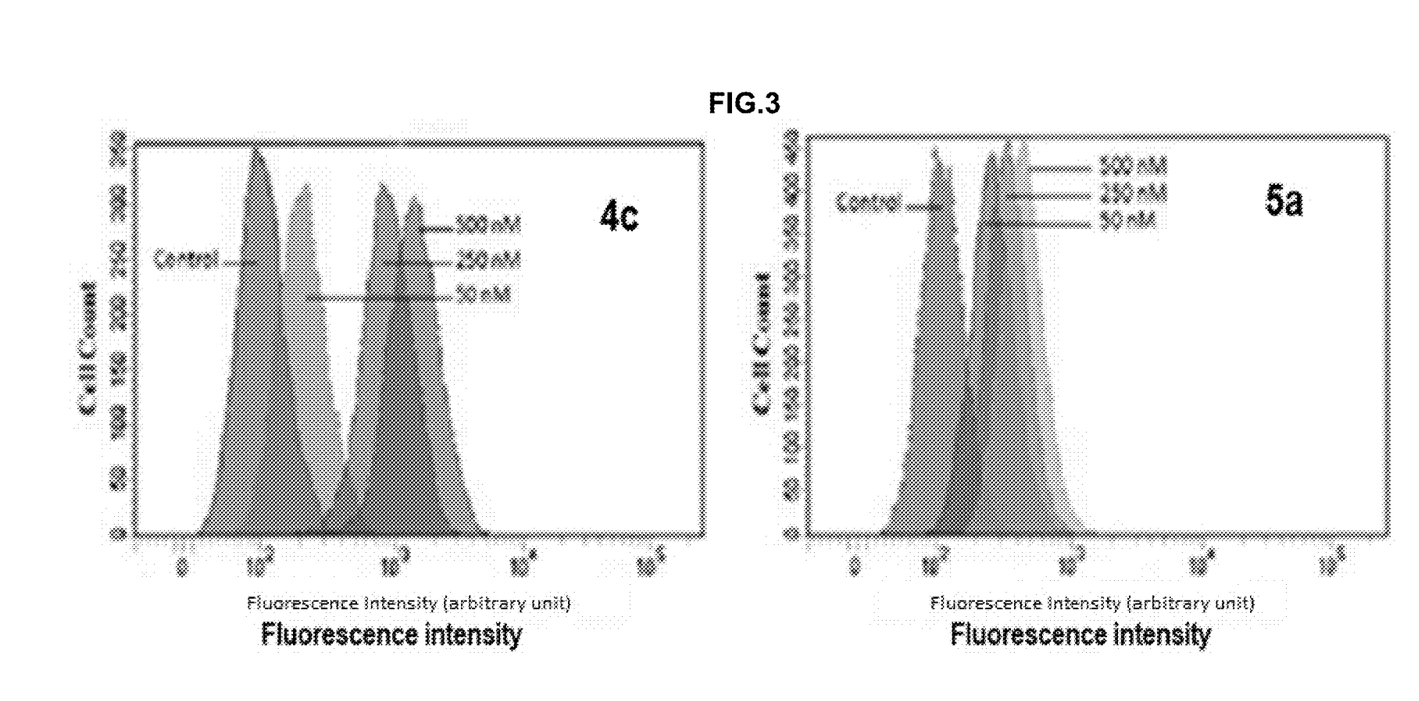
FIG. 3: illustrates FACS data in CHO-K1 cells.

Thus when several hydrophobic and/or lipophilic groups was tested it was thus surprisingly found that hydrophobic or lipophilic groups including tert-butyloxycarbonyl [t-BOC], hexafluoro-iso-propyloxycarbonyl [i-Pr(F)] were effective for permealization of the transporter 4. Though 4c and 5a both have same number of inter guanidinium linkages (four) but 4c internalizes better than 5a as observed by FACS analysis in CHO-K1 cells (FIG. 3) and also in both live cells and paraformaldehyde fixed cells. At 500 nM concentration, 4c internalized 99.9% in CHO-K1, PC-3, A-549, MCF-7 cells whereas 5a internalized only 83%. Thus it can be concluded that only internal guanidinium groups are not sufficient to improve the cellular internalization. All the experiments were done in the presence of 10% serum-containing media. When $R_1$=H in 4, 1.1% cellular uptake was observed in FACS data. Interestingly, it was found that $R_1$=hexafluoroisopropyloxy carbonyl (i-Pro(F)), 4d internalized 99.8% even at low concentrations as low as 150 nM under the similar conditions. It can be now clearly inferred that hydrophobic/lipophilic group has a surprisingly important role for improved cellular permealization though number of inter guanidinium linkages are same. In comparison with FIG. 1 compounds of co-pending 71/KOL/2013, the internalization concentration was 2.5 µM for 1 and also in the absence of serum. Molecular docking studies in the water lipid interface supported that presence of hydrophobic chain at the N-terminal is necessary as it has interactions with the lipid chain during cell penetration and there is a conformational change of the transporter during penetration. Toxicity study of 4a was carried out using MTT assay and it shows almost no toxicity upto 100 µM concentration whereas type 1 compound in FIG. 1, shows 90% survivability at 2.5 µM concentration only and 10% cells dead at even 40 fold lower concentration than that of 4a. In the context of exploring a useful molecular transporter which has a balance hydrophilic and hydrophobic character or has amphipathic character and in ideally having no toxicity, the molecule of the present invention of 4a/4b is thus a significant achievement. Thus the molecular transporter such as compound 4a/4b of the present invention meets the need of the day which has a balance of hydrophilic and hydrophobic or has amphipathic character and ideally in having no toxicity, is the first ever transporter which does not have any toxicity upto 100 µM concentration that too involving fewer number of guanidinium groups, only four.

Figure 4:
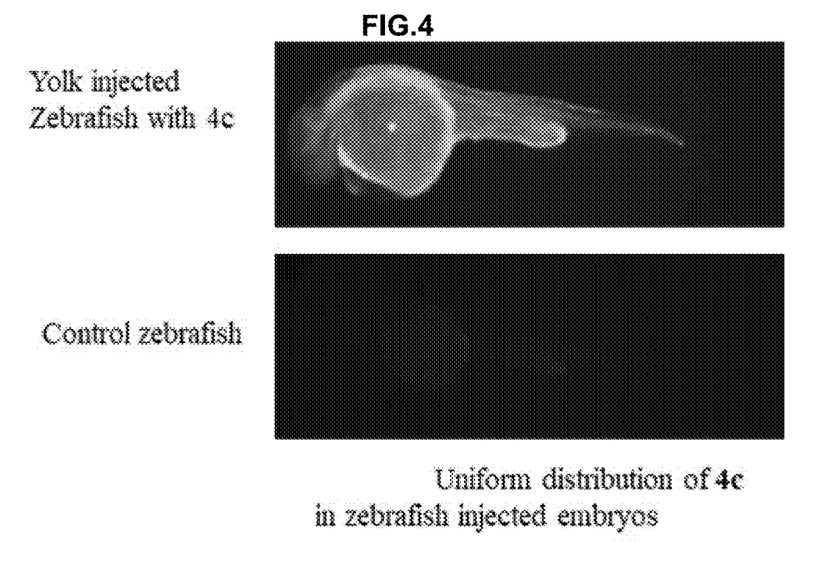
FIG. 4: illustrates uniform distribution of compound 4c in zebrafish injected embryos.

Further application of 4c as a carrier, it has shown a uniform distribution throughout the organism in zebrafish embryos when it is injected into the embryos at any stages as shown in FIG. 4 upper portion (yolk injected zebra fish with 4c) as against the control zebrafish shown in the lower portion of FIG. 4 and is thus useful for in vivo cargo delivery.

Figure 5:
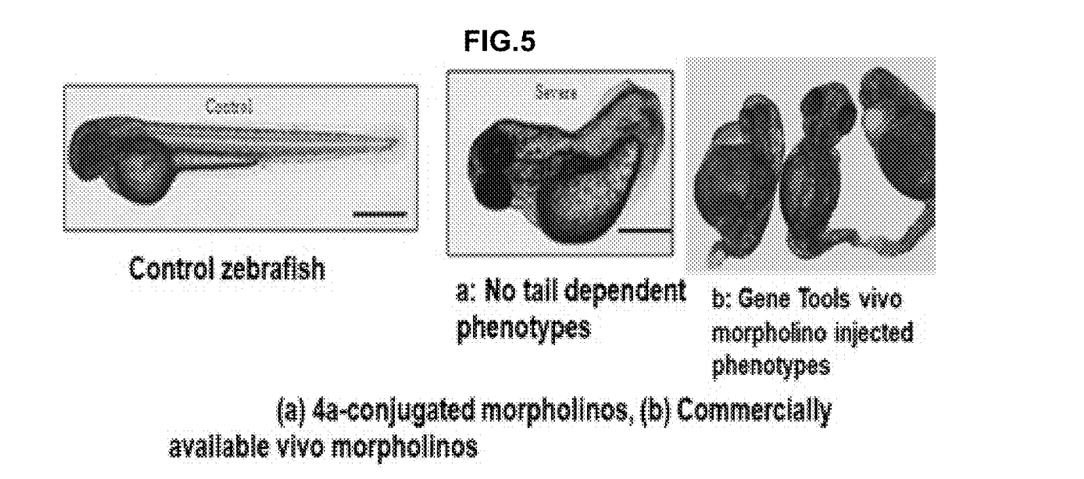
Figure 6:
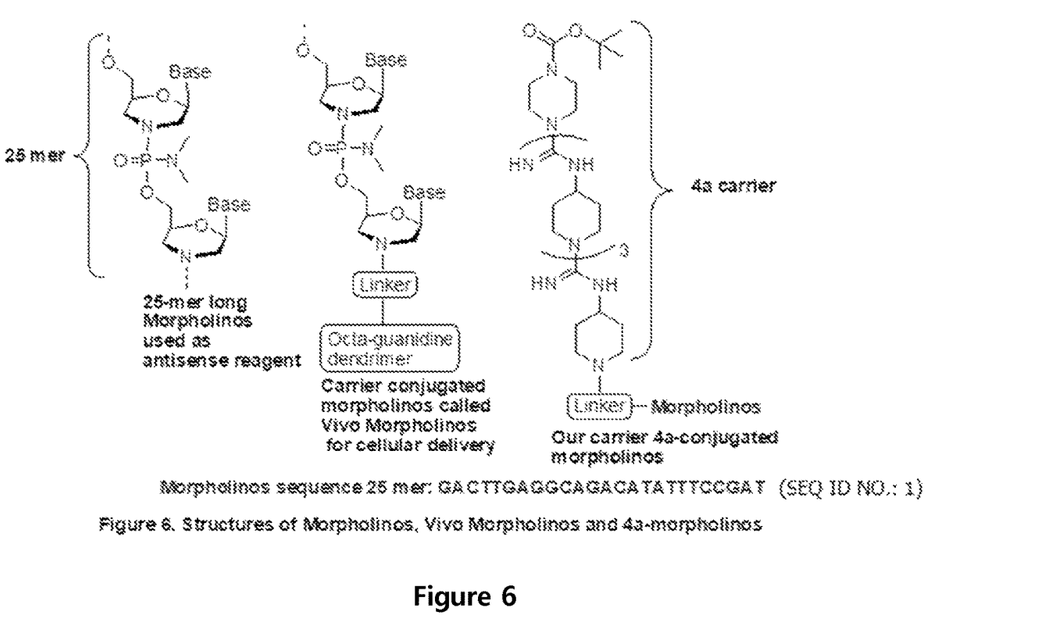
FIG. 6: illustrates representative structures of morpholinos, vivo morpholinos and oligo-guanidine structure 4a conjugated morpholinos.
Figure 7:
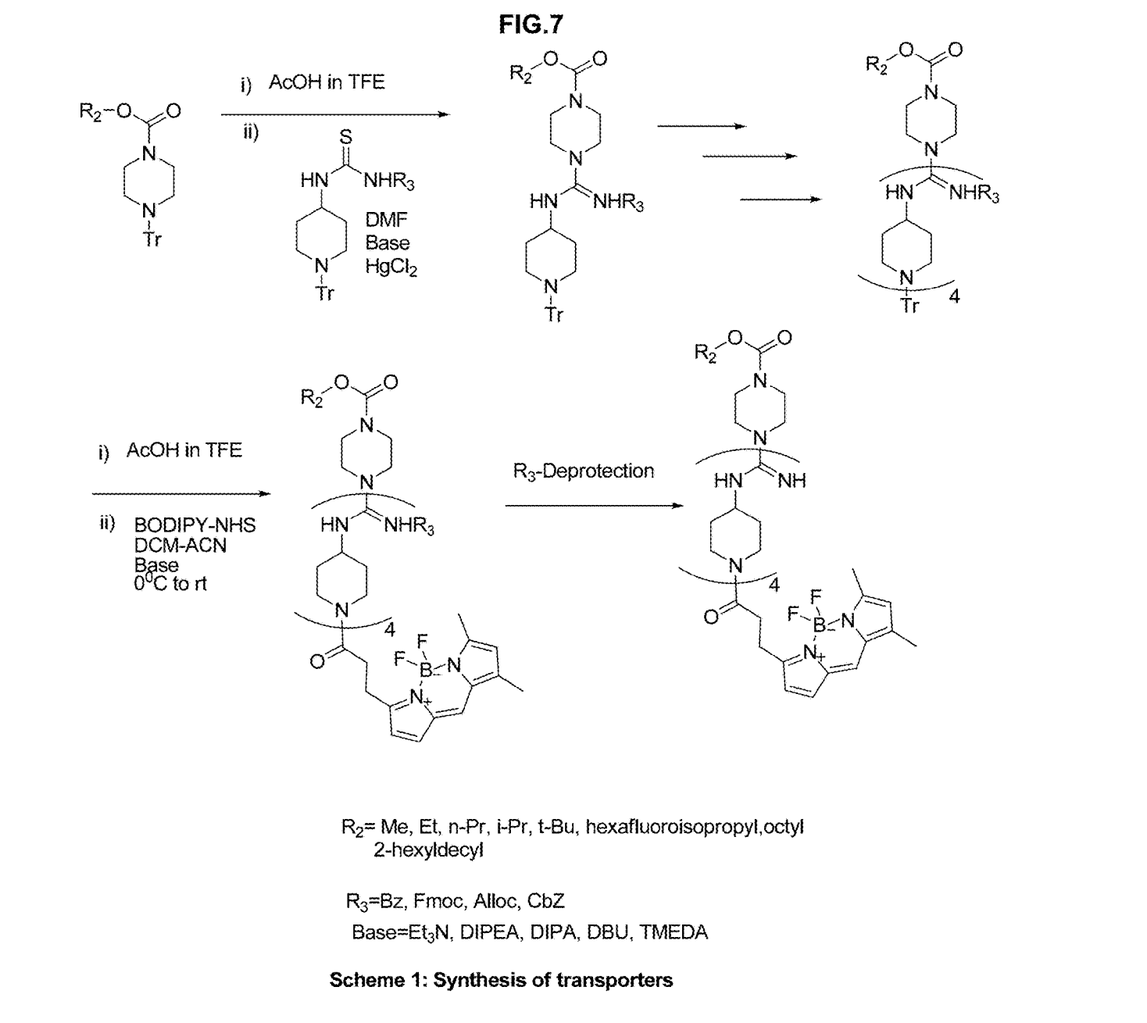
FIG. 7: illustrates the schematics for the synthesis of transporters Type 1.

Further application of 4c comprise, conjugating 4c with a 25-mer long known antisense reagent called morpholino oligonucleotides for gene silencing in zebrafsih model, which silenced the gene called no tail gene in different developmental stages. No tail dependent phenotypes were observed (FIG. 5). In the case of Gene tool vivo morpholinos (Vivo morpholinos from Gene Tools LLC is the only commercialized patentable technology, costing 700 $ for 400 nmol, www.gene-tools.com) injected embryos, the characteristic of the phenotypes were not identical as reported whereas the 4a-conjugated morpholinos of the present invention shows identical phenotypes (gene specific phenotypes), which is due to the involvement of high level toxicity of the carrier attached with the vivo morpholinos the reason due to which vivo morpholinos do not have any applications in zebrafish for embryological studies. It is very important to mention here that such conjugated morpholino oligonucleotides of the present invention worked much better than commercially available Vivo morpholinos from Gene Tools LLC (that is the only patentable technology commercialized, cost is 700 $ for 400 nmol, www.gene-tools.com). Toxicity of 4a conjugated morpholino was compared with Gene Tools vivo morpholinos and it was found that the 4a conjugated morpholinos shows in MTT assay almost no toxicity upto 100 µM where as Gene Tools vivo morpholinos shows toxicity from 20 µM, cells survived only 60% and looked round yellowish. Structures of morpholinos, vivo-morpholinos and carrier 4a conjugated morpholinos of the present invention are illustrated in FIG. 6.

Example 2: Synthesis of the Cellular Transporters

To a stirred solution of carbamate in TFE (trifluoroethanol), was added AcOH at 0° C. and the reaction mixture was left for half an hour. Then the resulting amine was reacted with protected thiourea monomer to get the dimer. The trityl deprotection followed by reaction with said thiourea monomer was repeated until the pentamer was obtained. The trityl group was deprotected and the resulting free amine was conjugated with BODIPY-NHS ester in presence of base in DCM-ACN (dichloromethane-acetonitrile). Finally the Fmoc groups were deprotected using 20% piperidine in DMF (dimethylformamide) to get the desired transporter which was purified and dissolved in HPLC water to prepare the stock according the absorbance of the BODIPY conjugated transporter. All the transporters were synthesized using the same procedure starting from the corresponding carbamates.

Figure 8:
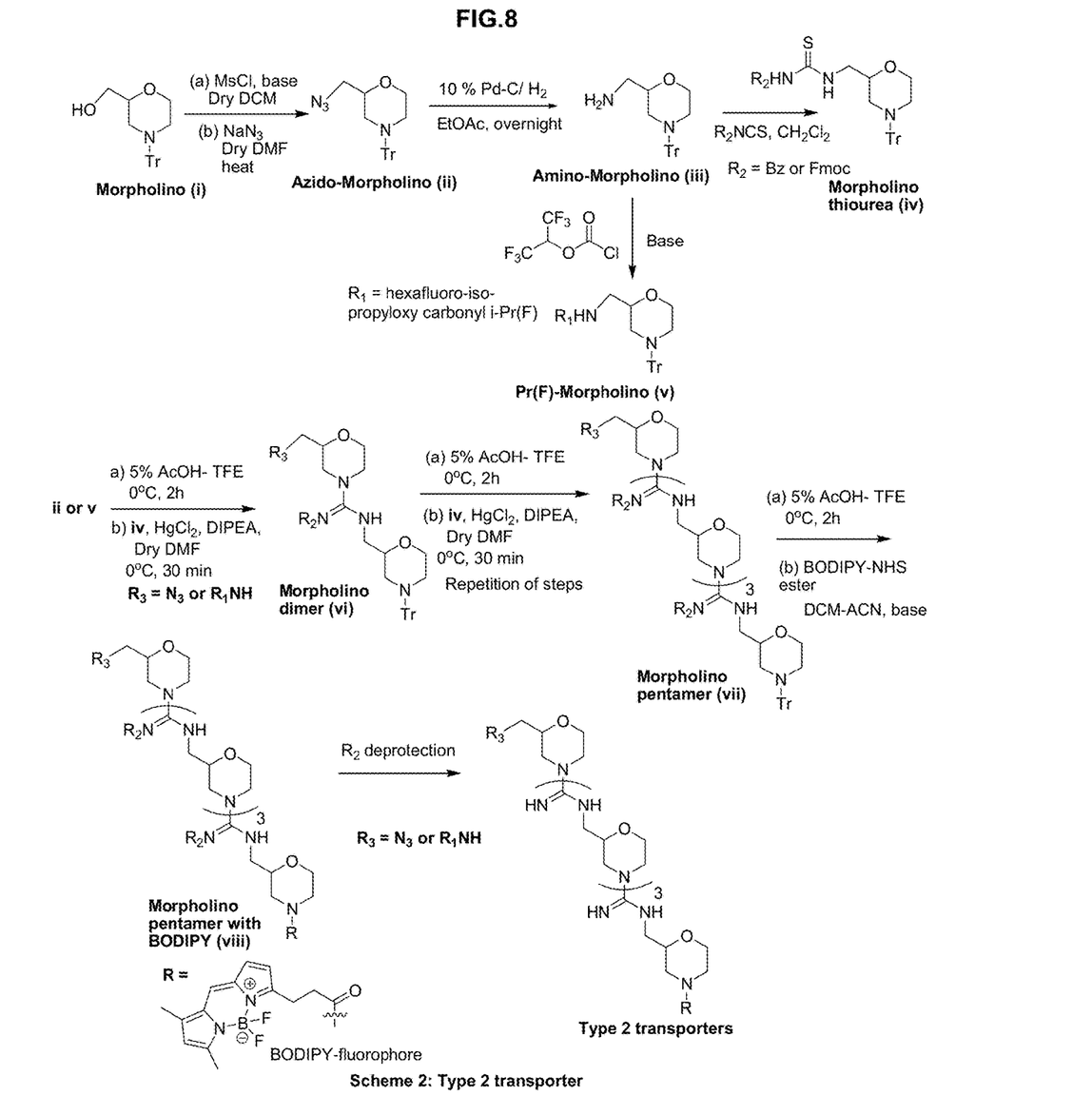
FIG. 8: illustrates the schematics for the synthesis of transporters of Type 2.

Transporters of type 2 were synthesized in the same procedure once the Tr-protected azido morpholino (ii) or i-Pr(F)-protected Tr-morpholino (v) were synthesized by standard procedures and the thiourea derivative was used for coupling as per FIG. 8.

Synthesis of 4a-conjugated antisense of FIG. 6 which is the synthesis of transporter (4a) conjugated morpholino antisense oligo (25 mer) was performed using click reaction in the following steps (a) providing molecule 4a for reaction with NHS-ester of 3-azido propanoic acid in the presence of base in acetonitrile to obtain azido-functionalized transporter of 4a;

(b) providing 25-mer morpholino oligo for reaction with NHS ester of 5-hexynoic acid in sodium bicarbonate buffer to obtain alkyne-conjugated morpholino oligo;

(c) reacting the alkyne-conjugated morpholino oligo with azido-functionalized transporter of 4a in the presence of Cu (I) catalyst (using click reaction) to obtain transporter conjugated morpholino oligomer of 4a as in FIG. 6.

The conjugated morpholino oligo was purified by HPLC using C-18 column.

Example 3: Cellular Uptake Study

To study the quantitative cellular uptake Chinese hamster ovary (CHO-K1) cells were treated with BODIPY conjugated transporters in 10% serum containing medium. After 4 h incubation fluorescence activated cell sorting (FACS) studies were carried out. From the result it was found that transporter 4d with i-Pr(F)-protection showed 98.6%, 99.8%, 99.9% cellular uptakes at 50 nM, 150 nM, 250 nM concentrations respectively. The transfection efficiency of other transporters (4c, 4e-4j and 5) were much lower than 4d while the cellular uptakes ranged from only 40% to 95% at the aforesaid concentrations studied. The best one is 4d followed by 4c, internalises 99.9% at 500 nM concentration.

It is thus possible by way of the present advancement to provide for oligo-guanidines based cellular transporter comprising heterocyclic rings of FIG. 2 including 4-aminopiperidine, piperazine, morpholine having at least one N-terminal tailored with hydrophobic and/or lipophilic group and related compounds as per FIG. 2. The cell penetrating agents/carriers having a balance of hydrophilic and hydrophobic or has amphipathic character and ideally in having no toxicity as disclosed in FIG. 2, is the first ever transporter which does not have any toxicity upto 100 µM concentration that too in involving only fewer number of guanidinium groups.

A sequence listing electronically submitted with the present application on Mar. 27, 2020 as an ASCII text file named 20200327_P97718AS03_TU_SEQ, created on Mar. 23, 2020 and having a size of 1,000 bytes, is incorporated herein by reference in its entirety.

We claim:

1. An oligo-guanidine as a cell penetrating agent or a carrier, represented by the following formula:

wherein $R_1$ is selected from the group consisting of hydrophobic and lipophilic groups of tert-butyloxycarbonyl (t-BOC), hexafluoro-iso-propyloxycarbonyl [i-Pr(F)], n-octyloxycarbonyl (n-OOC), 2-hexyl-1-decyloxycarbonyl (HDOC), methoxycarbonyl (MeOC), ethoxycarbonyl (EtOC), propoxycarbonyl (POC), and iso-propoxycarbonyl (IPOC);

R is a molecule selected from the group consisting of fluorophore, peptide, a diagnostic agent, a probe, an antisense agent, or a cancer drug; and n is an integer from 1 to 4.

2. A method of transporting a molecule into a cell comprising providing the oligo-guanidine of the formula according to claim 1, thereby transporting the molecule into the cell.

* * * * *